United States Patent [19]
Chan

[11] Patent Number: 5,810,824
[45] Date of Patent: Sep. 22, 1998

[54] SURGICAL FASTENER ASSEMBLY AND METHOD FOR BONE FRACTURE FIXATION

[76] Inventor: Kwan-Ho Chan, 4803 First Pl., Lubbock, Tex. 79416

[21] Appl. No.: 800,920

[22] Filed: Feb. 13, 1997

[51] Int. Cl.⁶ .................................................. A61B 17/82
[52] U.S. Cl. .............................. 606/70; 606/74; 606/103
[58] Field of Search ................... 606/74, 72, 73, 606/61, 103, 60, 69, 70, 71

[56] References Cited

U.S. PATENT DOCUMENTS

| | | | |
|---|---|---|---|
| 4,119,091 | 10/1978 | Partridge | 606/74 |
| 4,805,602 | 2/1989 | Puno et al. | 606/61 |
| 5,190,545 | 3/1993 | Corsi et al. | 606/74 |
| 5,324,291 | 6/1994 | Ries et al. | 606/71 |
| 5,443,382 | 8/1995 | Stone et al. | 606/232 |
| 5,466,237 | 11/1995 | Byrd, III et al. | 606/61 |
| 5,607,430 | 3/1997 | Bailey | 606/74 |
| 5,653,711 | 8/1997 | Hayano et al. | 606/74 |
| 5,665,089 | 9/1997 | Dall et al. | 606/71 |

*Primary Examiner*—Guy V. Tucker
*Attorney, Agent, or Firm*—Pandiscio & Pandiscio

[57] ABSTRACT

A surgical fastener assembly for use in bone fracture fixation comprises an adapter, a surgical cable, a compression plate, and a crimp device, the adapter having a head portion having a bore extending therethrough adapted to receive the surgical cable, and a protrusion extending from an underside of the head portion and centrally of the head portion and adapted for insertion into a recess in the compression plate, the crimp device being deformable upon the cable to hold the cable in place around bone portions.

27 Claims, 11 Drawing Sheets

SURGICAL FASTENER ASSEMBLY AND METHOD FOR BONE FRACTURE FIXATION

FIELD OF THE INVENTION

This invention relates to surgical apparatus and procedures in general, and more particularly to fastening devices, such as crimp devices and adapters, for use with surgical cables and compression plates in fixation of bones during surgeries for fractured bone or bone reconstruction.

BACKGROUND OF THE INVENTION

Bone fracture fixation is an established art. Fixation screws and metal compression plates used in combination for fracture fixation are standard industry wide. The standards are based on designs developed by the Association for the Study of the Problem of Internal Fixation. Therefore, screws and plates made by one manufacturer are geometrically compatible with screws and plates of other manufacturers.

Surgical cables and metal compression plates, used in combination, and without fixation screws, are also well known in the art of fracture fixation. Cables and plates are generally used where the use of screws and plates is not suitable. By way of example, cables and plates are frequently used in fixation of long oblique fractures where the medullary canal has a metal prosthesis in place from prior surgery, such as a hip replacement. The bone cement and metal prosthesis within the bony canal preclude the use of screws for fixation in certain segments of the bone. Fixation with cables or wires is required in such cases. In bones that are osteoporotic, where screw fixation is not practical, fixation with cables or wires is required. Such cables are further used in conjunction with screws and plates, as for example, when the screw strips its threads in deployment, or the screw alone is otherwise deemed insufficient for the fixation at hand. In some instances, it is helpful to omit the metal compression plate altogether and secure a fracture with only cables, with no screw and no plate.

The cables are used to encircle the bone, or bone and plate, to provide for fixation. In fixation by cable, it is customary to use a fastening device, typically a crimp device which is adapted to be deformed upon the cable for securing the cable in place, encircling the bone in the fracture area. In other fastening devices of this type, the cable is fixed in the fastening device by a holding screw, or by welding, or the like. In general, fixation with cable on the shaft of long bone does not present a problem with migration because the bone in this area is tubular in geometry. However, at the ends of long bone (known as the metaphysis), where there is a significant flare in the geometry, tightening the encircling cable or wire causes the cable and fastening device to migrate towards the narrower section of the bone. Such migration can displace the cable and fastening device from its intended location sufficiently to weaken, or render ineffective, encirclement of the fracture.

To prevent migration of fasteners, some compression plates are provided with slots for receiving and retaining the fastener devices. However, the provision of such a slot renders the location of a screw hole in the same area impractical, and a surgeon is unable to apply a fixation screw in the area of a fastener slot and unable to use a fastener in the area of a screw hole.

Thus, there is a need for an improved fastener assembly, including an adapter for use with known metal compression plates for fixation of bone fractures, and a need for such an adapter as may be used in conjunction with conventional screws and plates in combination. There further exists a need for a fastener assembly for use in fixation of metaphyseal bone without the use of a metal plate. There still further exists a need for such fastener assemblies as will not slide along a compression plate or bone during tightening of the cable during cable deployment.

OBJECTS OF THE INVENTION

Accordingly, one object of the present invention is to provide an improved fastener assembly for use in surgical fracture fixation.

Another object of the present invention is to provide an improved fastener assembly which includes known metal compression plates and cables for bone fracture fixation, and which does not slide along the plate during tightening of the cable.

Still another object of the present invention is to provide an improved fastener assembly adapted for use with known metal plates and cables and further adapted for use with standard bone fixation screws.

A further object of the invention is to provide a method for effecting bone fracture fixation.

SUMMARY OF THE INVENTION

These and other objects of the present invention are addressed by the provision and use of a novel surgical fastener assembly, including an adapter for use in bone fracture fixation, the adapter comprising a head portion having at least one bore extending therethrough and adapted to receive surgical cable, a protrusion extending from an underside of the head portion and centrally of the head portion, and adapted for insertion into a compression plate screw hole recess, and a discrete crimp device for fixing the cable around the bone fracture.

The objects of the present invention are further addressed by the provision and use of a novel surgical fastener assembly, including an adapter for use in bone fracture fixation, the adapter comprising a head portion having at least one bore extending therethrough and adapted to receive surgical cable, a protrusion extending from an undersurface of the head portion and centrally of the head portion, a fixation screw having a head portion having an axial hole therein, the hole being adapted to receive the protrusion, and a discrete crimp device for fixing the cable around the bone fracture.

The objects of the present invention are still further addressed by the provision of a novel method for effecting bone fracture fixation.

The above and other features of the invention, including various novel details of construction and combinations of parts, will now be more particularly described with reference to the accompanying drawings and pointed out in the claims. It will be understood that the particular devices, assembly, and method embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
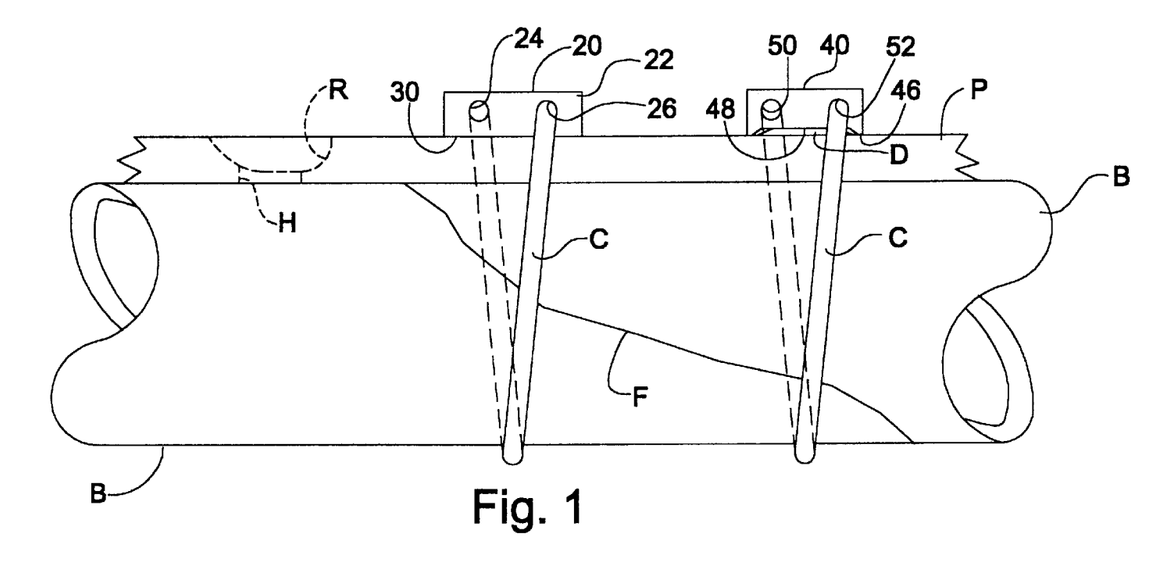
FIG. 1 is a side elevational view of a fractured bone, a compression plate, surgical cables, and first and second embodiments of fastener devices in accordance with the present invention.
Figure 2:
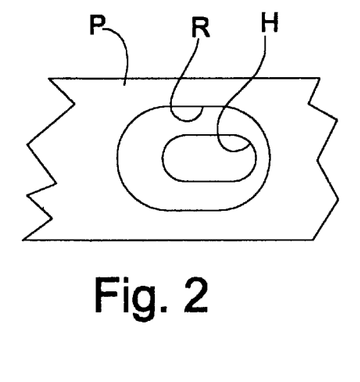
FIG. 2 is a top plan view of a portion of the compression plate of FIG. 1.

Referring to FIG. 1, there is shown a bone B having a fracture F therein. A compression plate P and surgical cable C are applied to bone B in the area of fracture F to bind together the segments of bone B, all in accordance with prior art teachings. The plate P is provided with a screw hole recess R (FIGS. 1, 2, 5 and 7) and extending therefrom an elongated screw hole H.

In accordance with the present invention, there is provided an improved fastener device, illustrated in the form of a crimp device 20, for receiving and retaining cable C. Crimp 20 is of a deformable material, preferably metal, and in particular stainless steel, and includes a top block portion 22 having first and second bores 24, 26 extending entirely therethrough from side-to-side and parallel to each other, and adapted to receive and retain surgical cable C. When the fastener device is intended to have cable C welded therein, or retained by one or more screws, or the like, the top block portion 22 obviously need not be deformable.

Figure 5:
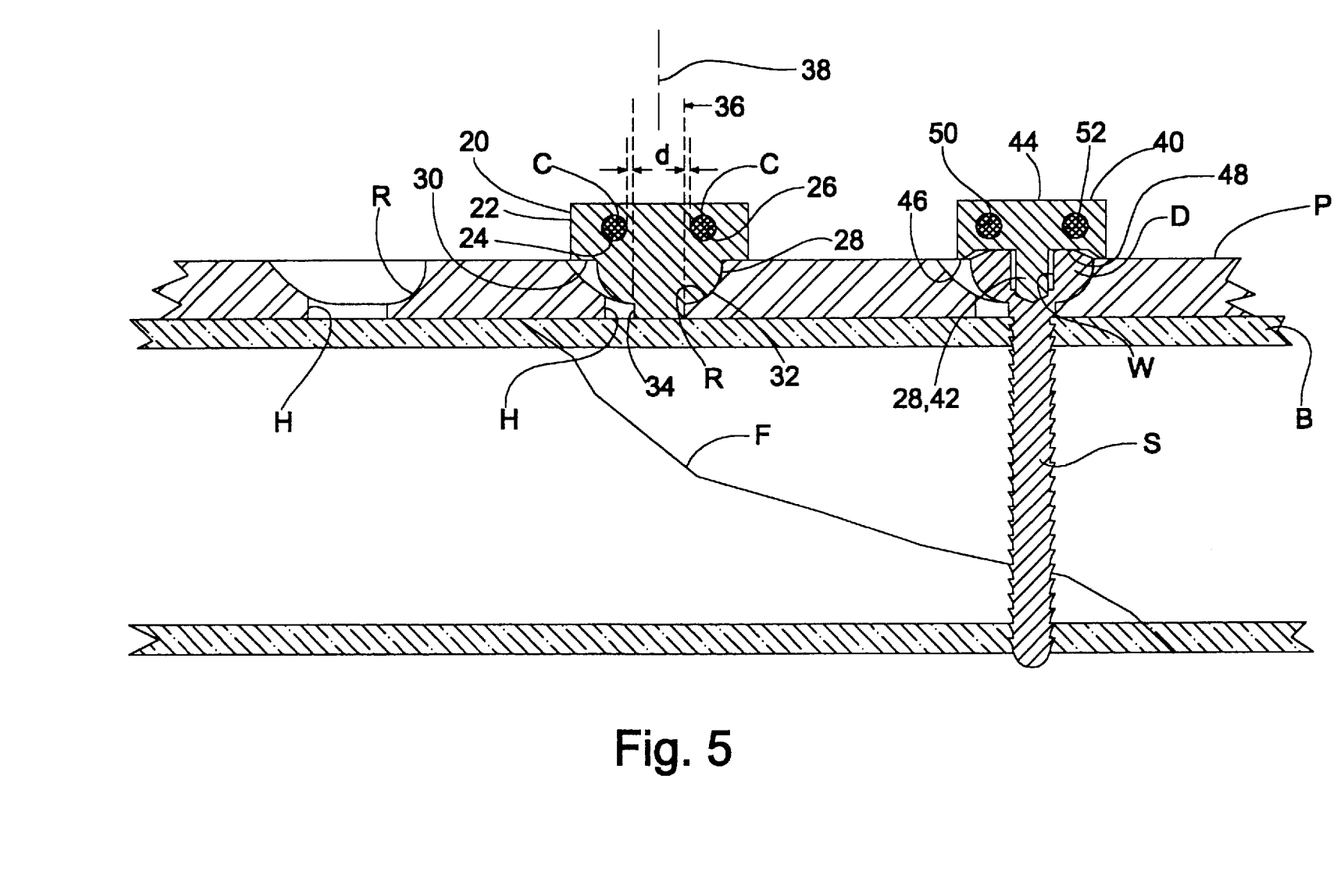
FIG. 5 is similar to FIG. 1, but shows the bone, compression plate and fastener devices in section.

A protrusion 28 (FIGS. 3, 5 and 7) extends from an underside 30 of top block portion 22 centrally of top block portion 22. In a first embodiment, shown in FIGS. 3, 5 and 7, protrusion 28 includes a bulbous portion 32 depending from underside 30 of top block portion 22, and a cylindrical portion 34 depending from the bulbous portion 32 and centrally thereof. As shown in FIG. 5, bulbous portion 32 is configured and adapted for disposition in recess R of plate P, and cylindrical portion 34 is configured and adapted for disposition in screw hole H of plate P.

Figure 3:
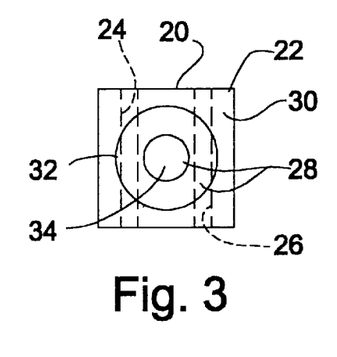
FIG. 3 is a bottom plan view of the first embodiment of fastener device shown in FIG. 1.
Figure 4:
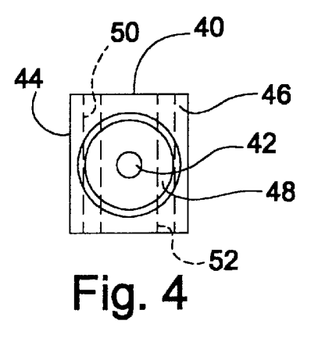
FIG. 4 is a bottom plan view of the second embodiment of fastener device shown in FIG. 1.

As may be seen in FIG. 3, bulbous portion 32 and cylindrical portion 34 of protrusion 28 are circular in bottom plan view, and therefore circular in widthwise cross-section and, as noted above, centered with respect to top block portion 22, such that protrusion 28 is permitted to rotate in plate recess R and screw hole H of plate P.

As may be seen in FIG. 5, first and second bores 24, 26 are disposed equal distances d from, and on opposite sides of, a hypothetical extension 36 of cylindrical portion 34 of protrusion 28 through top block portion 22. Bores 24, 26 extend normal to a lengthwise axis 38 of cylindrical portion 34.

In operation, the segments of bone B are placed together in abutting relationship along the line of fracture F. A compression plate P is placed alongside, and in engagement with, bone B, extending over both segments of bone B (FIGS. 1 and 5). At least one fastener device, such as crimp 20, is placed in plate screw hole recess R (FIG. 5). Cable C is extended through one of the bores 24, 26, around bone B (FIG. 7) and through the other of bores 24, 26. The cable is drawn taut and the crimp device is crimped (not shown), using crimping tools of the type known in the art. Again, the fastener may include means for fixing cable C to the fastener other than by crimping, in which case such other fixing means is utilized in place of crimping. Alternatively, crimping or other fastening means may be applied to cable C independently of device 20, as will be described hereinbelow.

In the course of tightening the cable C, the bores 24, 26, extending parallel to each other, normal to protrusion axis 38, and equidistant from the hypothetical extension 36 of cylindrical portion 34, are turned in plate screw hole recess R and screw hole H to assume the shortest distance between opposed exposed portions of cable C. The crimp device 20 thereby obviates subsequent loosening of cable caused by the crimp device gradually acceding to cable forces urging the crimp to assume the shortest distance between the exposed cable portions.

Figure 6:
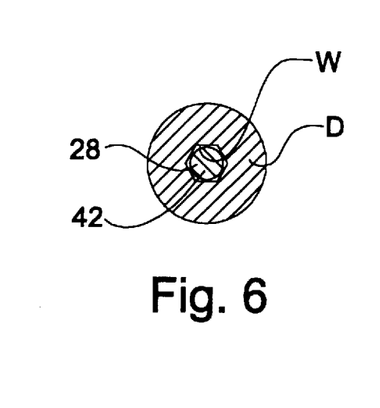
FIG. 6 is a widthwise sectional view of a portion of the second embodiment of fastener device disposed in a portion of a fixation screw.
Figure 7:
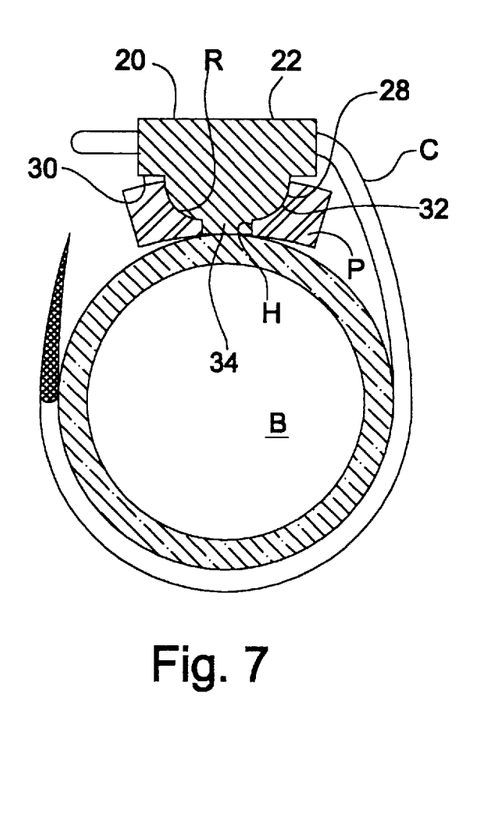
FIG. 7 is a sectional view normal to the section of FIG. 5, illustrating use of the first embodiment of fastener device.
Figure 8:
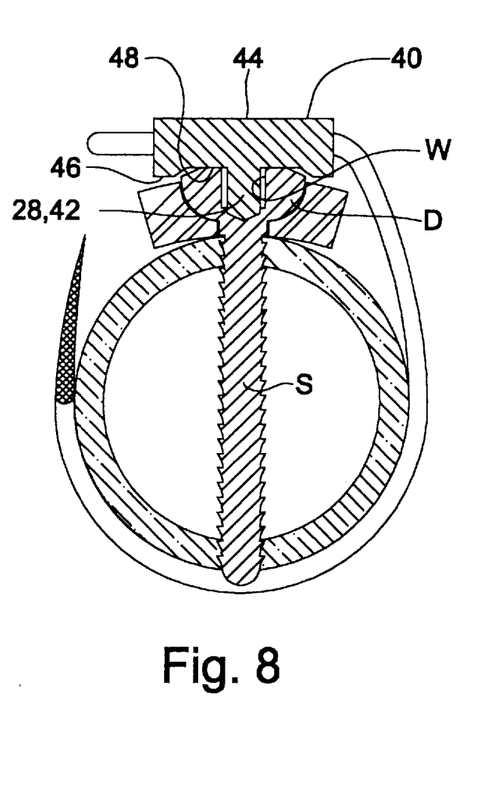
FIG. 8 is a sectional view normal to the section of FIG. 5, and similar to FIG. 7, illustrating use of the second embodiment of fastener device.

In FIGS. 1, 4, 5 and 8, there is shown an alternative embodiment of crimp device 40 configured and adapted for use in conjunction with a fixation screw S having a head portion D with a hexagonally shaped wrench hole W therein (FIG. 6). Crimp 40 is similar to crimp 20, differences being (1) protrusion 28 comprises a cylindrical portion 42 configured and adapted for disposition in wrench hole W in screw head D, and (2) a top block portion 44, on underside 46 thereof, is provided with a recess 48 for receiving fixation screw head D. Crimp 40 is rotatable in screw head wrench hole W. Bores 50, 52 are disposed in top block portion 44 relative to a hypothetical extension of cylindrical portion 42 substantially the same as bores 24, 26 relative to the hypothetical extension 36 of cylindrical portion 34 of the above-described first embodiment. Crimp device 40 preferably is of metal, such as stainless steel.

In use of the second embodiment of crimp 40, fixation screw S is deployed as is customary in the art and crimp 40 is inserted into screw head D. Upon tightening of cable C, crimp 40 is rotatably drawn into providing the shortest distance between exposed portions of cable. Again, while referred to and described as a crimp device, it will be apparent that the fastener device 40 need not depend upon crimping, but may serve the intended purpose by utilizing any of the fixing means, other than crimping, described hereinabove; or alternatively, crimping or other means may be utilized independently of device 40.

Both the first and second embodiments of crimp device 20, 40 are retained by the compression plate recess R and hole H, and therefore refrain from migration along the plate P. Crimp devices 20, 40 may be used at any location on plate P where there is a recess R. Separate crimp recesses, or slots, are not required. Further, the second embodiment of crimp 40 is used in combination with a fixation screw.

Referring to FIG. 5, a comparison of the first and second embodiments of crimps 20, 40 reveals that protrusion 28 of first embodiment 20 is substantially of the same configuration as screw head D shown together with second embodiment 40.

Figure 9:
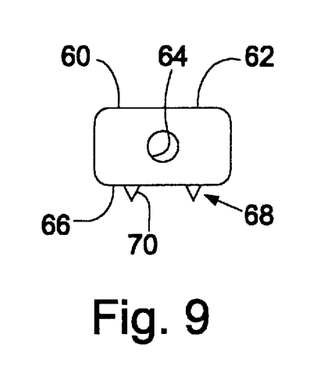
FIGS. 9–11 are side elevational views of variations of a third embodiment of fastener device.
Figure 10:
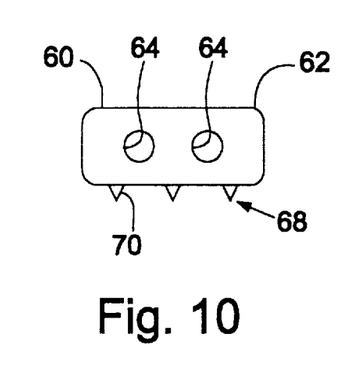
Figure 11:
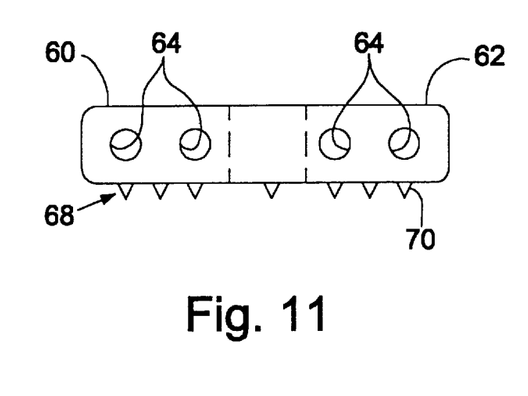
Figure 12:
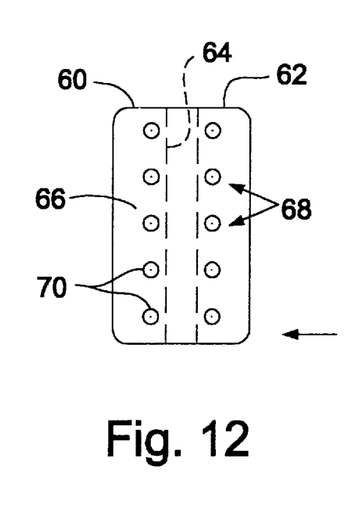
FIGS. 12–14 are bottom plan views of the respective fastener devices shown in FIGS. 9–11.
Figure 13:
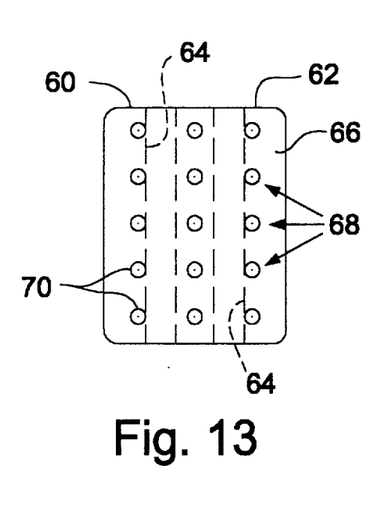
Figure 15:
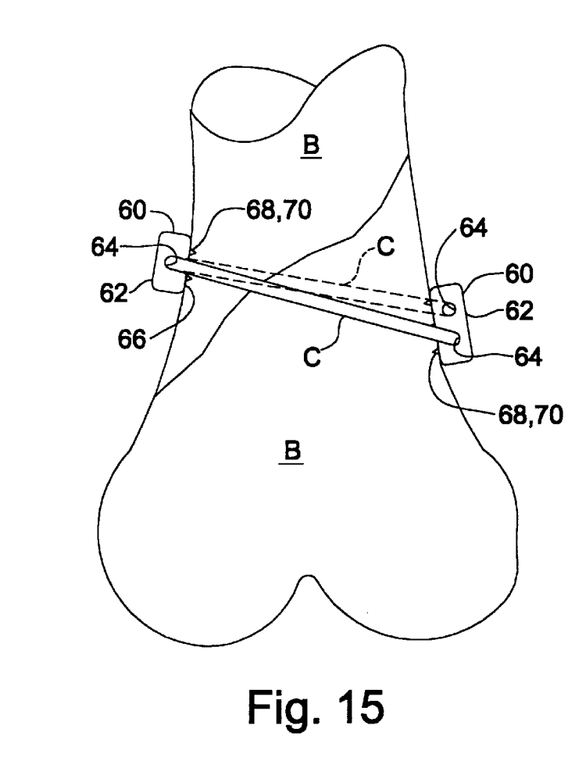
FIG. 15 illustrates diagrammatically typical use of the fastener devices of FIGS. 9, 12 and FIGS. 10, 13.

In FIGS. 9 and 12 there is shown another alternative embodiment of fastener device 60 comprising a block 62 having a bore 64 extending therethrough. An undersurface 66 of block 62 is provided with gripper means 68 thereon for engagement with a bone surface (FIG. 15). The gripper means 68 may comprise bone surface penetration means, such as spike-like elements 70, as shown in FIGS. 9 and 12, or may comprise other gripping means, such as a roughened surface, friction bands, and the like.

Figure 16:
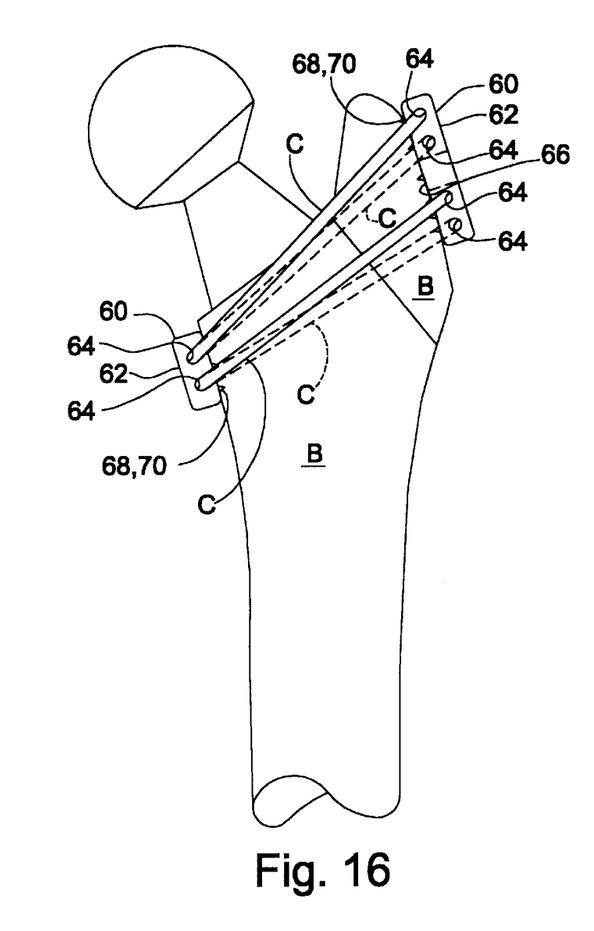
FIG. 16 illustrates diagrammatically typical use of the fastener devices of FIGS. 10, 13 and FIGS. 11, 14;.

In FIGS. 10 and 13, and 11 and 14, there are shown variations of the embodiment shown in FIGS. 9 and 12, having a plurality of bores 64 therethrough and larger undersurfaces 66 with increased areas of gripper means 68. Fasteners 60 are used without compression plates and are applied directly to bone, as shown in FIGS. 15 and 16. Various combinations of fasteners 60 may be used. In FIG. 15, there is illustrated fastener 60 of FIGS. 9 and 12 used in combination with fastener 60 of FIGS. 10 and 13. In this arrangement, wherein the fasteners comprise crimp devices, the crimping is effected on the larger crimp device. Similarly, in FIG. 16 there is illustrated the crimp of FIGS. 10 and 13 used in combination with the crimp of FIGS. 11 and 14. In this arrangement, the crimping is effected on the larger crimp device.

The crimps 60 preferably are of stainless steel, or a cobalt-chromium-molybdenum alloy, or a titanium alloy, and can be bent to conform to a bone contour and, thereafter, be deformed by a crimping tool (not shown) to capture the cable in the crimp device. It will be apparent that the compression plate P, fastener 20, 40, 60, cable C, and screw S must be of the same material, or of electrochemically compatible materials, to avoid deleterious galvanic action among the components. Inasmuch as most cables, plates, and screws are of stainless steel, it usually is preferable that the fastener devices be of stainless steel.

In use of crimps 60, tightening of cable C forces gripper means 68 into intimate contact with the surface of bone B. If gripper means 68 constitute bone surface penetration means, such as the spike-like elements 70 shown in FIGS. 9–16, the tightening of cable C serves to urge elements 70 into the bone B, to securely anchor the crimps 60 in the bone.

Figure 14:
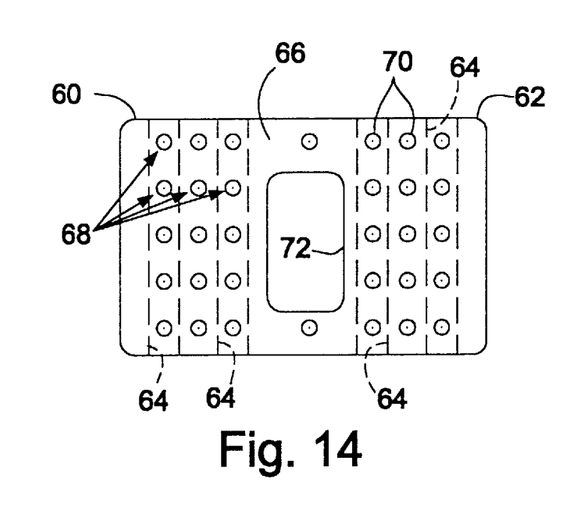

The crimp devices 20, 40, 60 may be provided with openings 72 (FIG. 14) which facilitate deformation of the crimp device and which, in the larger crimp devices, such as that illustrated in FIG. 14, serve to receive a crimping tool jaw (not shown).

As in the previous embodiment, the device 60 may be utilized simply as an adapter, and the fixation of the cables may be effected by other means independently of the adapter, either by crimping or otherwise.

Figure 17:
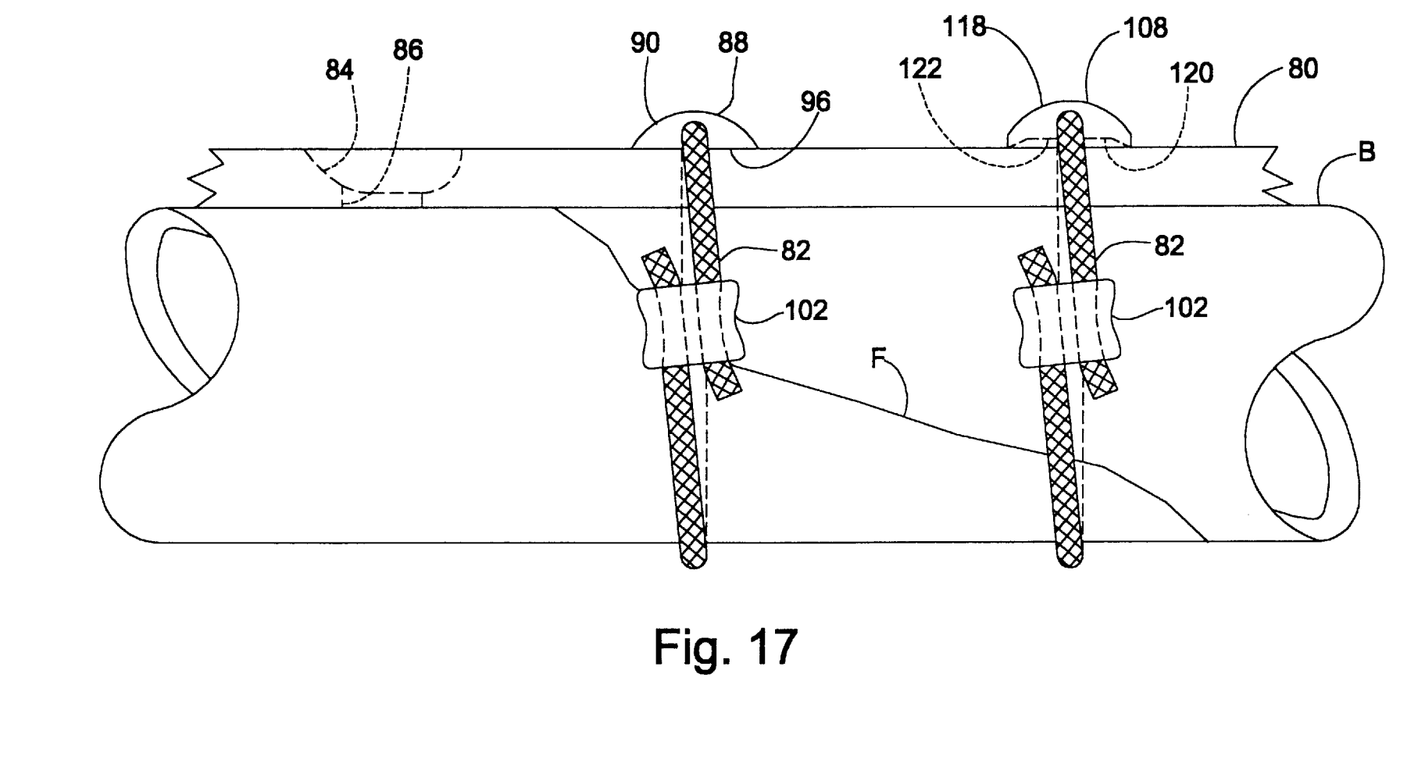
FIG. 17 is a side elevational view of a fractured bone, and bone fracture fixation assemblies including a compression plate, surgical cables, and two embodiments of adapter devices in accordance with the present invention.
Figure 18:
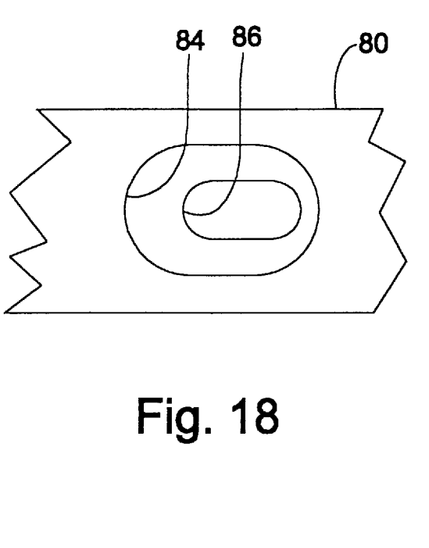
FIG. 18 is a top plan view of a portion of the compression plate of FIG. 17.

Referring, to FIG. 17, there is shown bone B having fracture F therein. A fastener assembly includes a compression plate 80 and surgical cable 82 which are applied to bone B in the area of fracture F to bind together the segments of bone B, all in accordance with prior art teachings. The plate 80 is provided with a screw hole recess 84 and extending therefrom an elongated screw hole 86.

Figure 19:
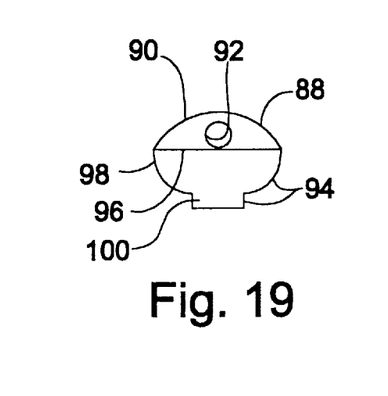
FIG. 19 is a side elevational view of one form of an adapter device for use as a component in the assembly of FIG. 17.

In accordance with the present invention, there is provided an improved fastener assembly, including the plate 80 and cable 82, and further including an adapter device 88, for receiving and retaining cable 82. The adapter device 88 preferably is of metal, such as stainless steel, and includes a head portion 90 having at least one bore 92 (FIGS. 19 and 20) extending entirely therethrough from side-to-side, and adapted to receive and retain surgical cable 82.

Figure 23:
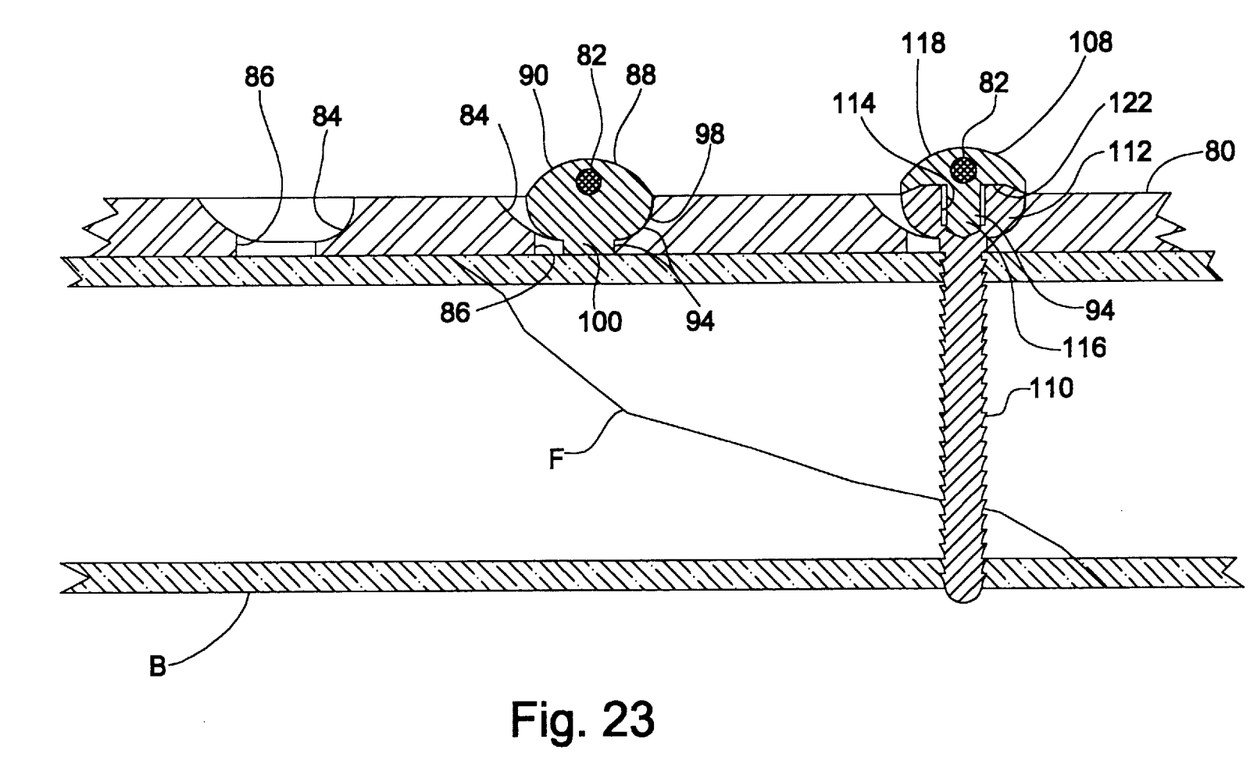
FIG. 23 is similar to FIG. 17, but shows the bone, compression plate, screw and adapter devices in section.

A protrusion 94 (FIG. 19) extends from an underside 96 of head portion 90 centrally of head portion 90. In one embodiment, shown in FIG. 19, protrusion 94 includes a bulbous portion 98 depending from underside 96 of head portion 90, and a cylindrical portion 100 depending from the bulbous portion 98 and centrally thereof. As shown in FIG. 23, bulbous portion 98 is configured and adapted for disposition in recess 84 of plate 80, and cylindrical portion 100 is configured and adapted for disposition in screw hole 86 of plate 80.

Figure 20:
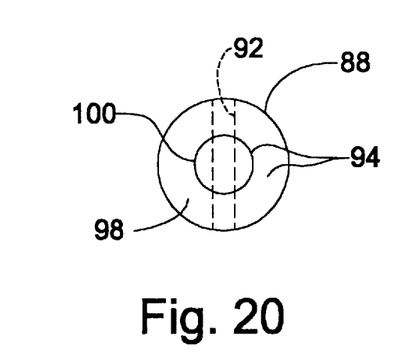
FIG. 20 is a bottom plan view of the adapter device of FIG. 19.
Figure 21:
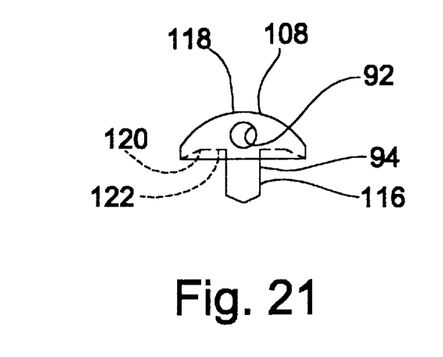
FIG. 21 is a side elevational view of an alternative form of adapter device.
Figure 22:
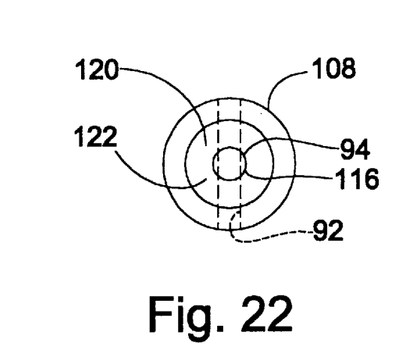
FIG. 22 is a bottom plan view of the adapter device of FIG. 21.

As may be seen in FIG. 20, bulbous portion 98 and cylindrical portion 100 of protrusion 94 are circular in bottom plan view, and therefore circular in widthwise cross-section and, as noted above, centered with respect to head portion 90, such that protrusion 94 is permitted to rotate in recess 84 and screw hole 86 of plate 80.

Referring again to FIG. 17, it will be seen that in this embodiment, the fastener assembly includes a discrete crimp device 102. The adapter device 88 does not function as a crimp device, but rather, the fixing of the cable 82 around the bone B is effected by the discrete crimp device 102.

In operation, the segments of bone B are placed together in abutting relationship along the line of fracture F. The compression plate 80 is placed alongside, and in engagement with, bone B, extending over both segments of bone B (FIGS. 17 and 23). At least one fastener device, such as adapter 88, is placed in plate screw hole recess 84 (FIG. 23). Cable 82 is extended through the bore 92, around bone B (FIG. 17) and through the crimp device 102. The cable 82 is drawn taut and the crimp device 102 is crimped, (i.e., deformed), using crimping tools of the type known in the art.

Figures 24, 25, 26:
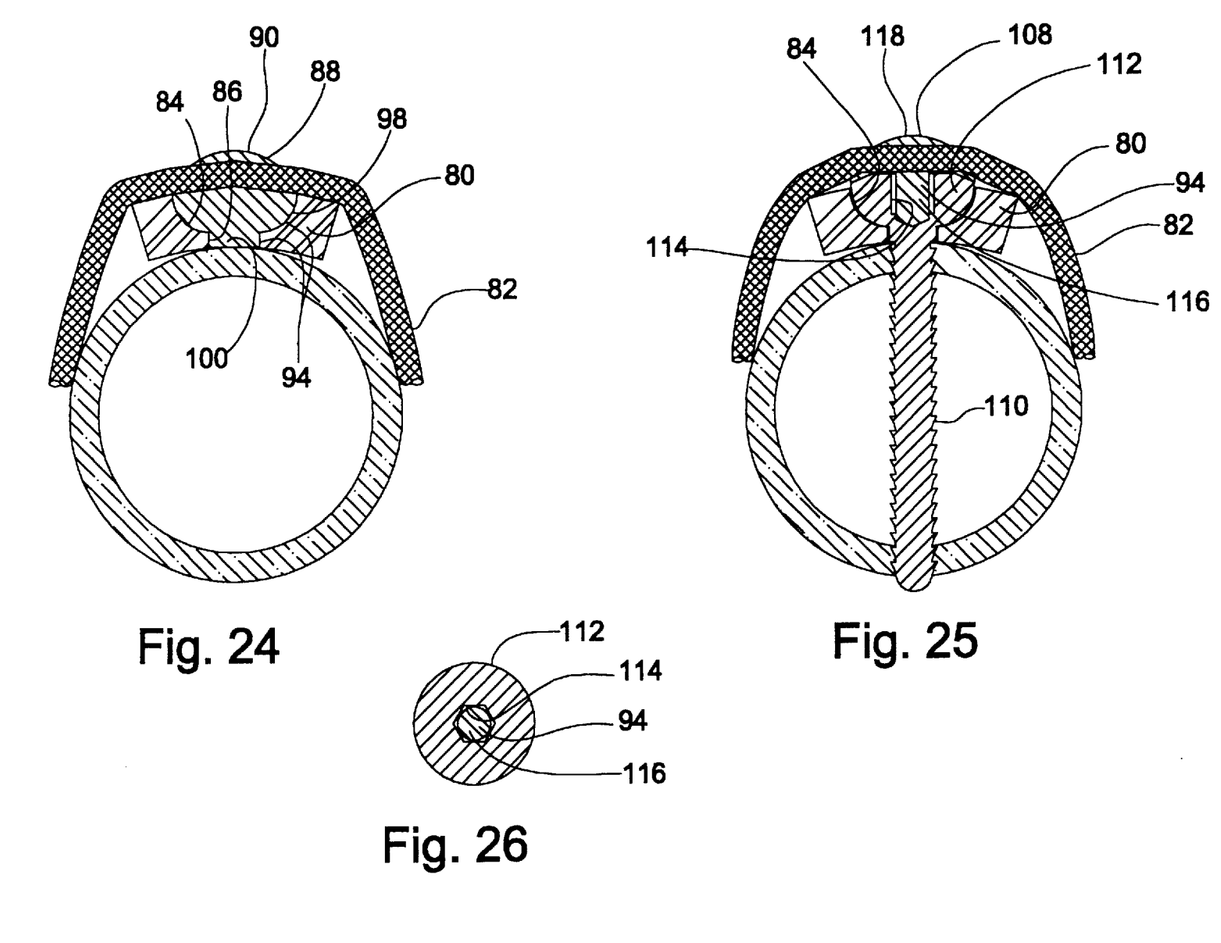
FIG. 24 is a widthwise sectional view of a portion of the adapter assembly of FIGS. 17, 19 and 20.
FIG. 25 is a widthwise sectional view of a portion of the adapter assembly of FIGS. 17, 21 and 22.
FIG. 26 is a widthwise sectional view taken through the screw head and adapter stem of FIG. 25.

In FIGS. 17, 23 and 25, there is shown an alternative embodiment of fastener assembly, including an adapter 108, and a fixation screw 110 having a head portion 112 with a hexagonally shaped wrench hole 114 therein (FIG. 26). Adapter 108 is similar to crimp 88, differences being (1) protrusion 94 comprises a cylindrical portion 116 configured and adapted for disposition in wrench hole 114 in screw head 112 and (2) a head portion 118 on underside 120 thereof, is provided with a recess 122 for receiving fixation screw head 112. Adapter 108 is rotatable in screw head wrench hole 114. Bore 92 is disposed in head portion 118 relative to a hypothetical extension of cylindrical portion 100 substantially the same as bores 24, 26 relative to the hypothetical extension 36 of cylindrical portion 34 of the above described first embodiment.

As in the case of the immediately previous embodiment (FIG. 24), in this embodiment (FIG. 25) the fastener assembly includes discrete crimp device 102 (FIG. 17).

In use of this embodiment of fastener assembly, fixation screw 110 is deployed as is customary in the art and adapter 108 is inserted in screw head 112. Cable 82 is fed through bore 92 and through crimp device 102. Cable 82 is tightened and crimp device 102 is crimped to lock cable 82 in place.

Figure 27:
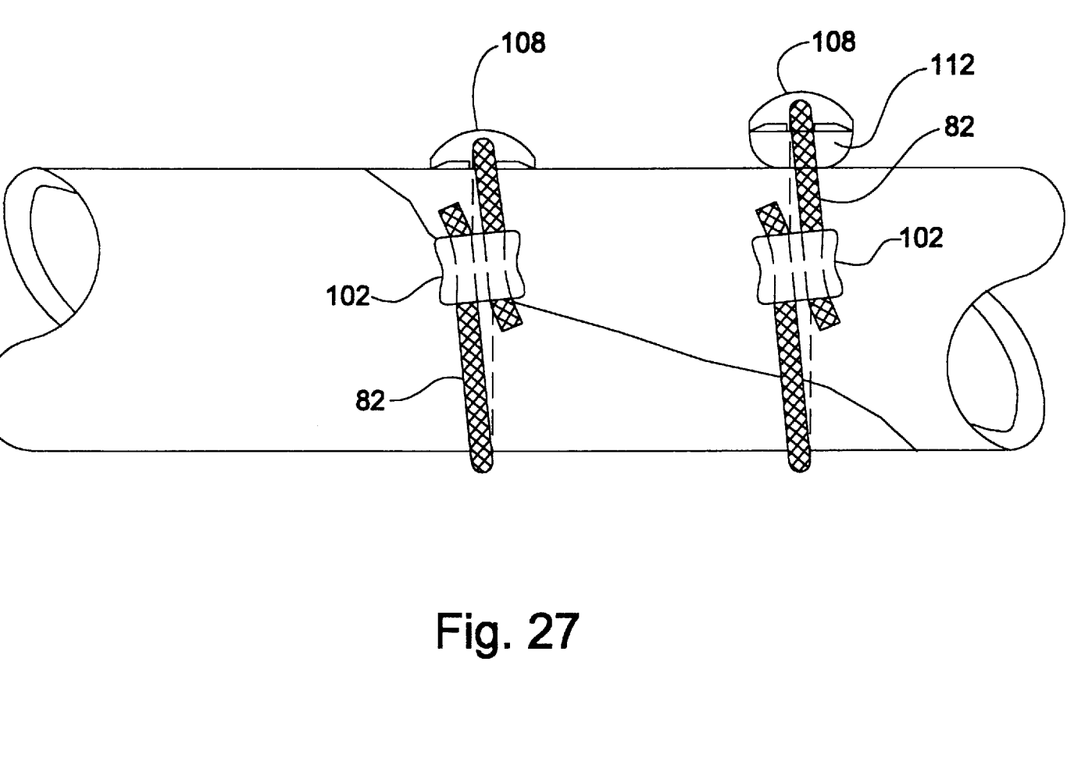
FIG. 27 is a side elevational view similar to FIG. 17, but showing one of the embodiments of FIG. 17, less the compression plate.
Figure 28:
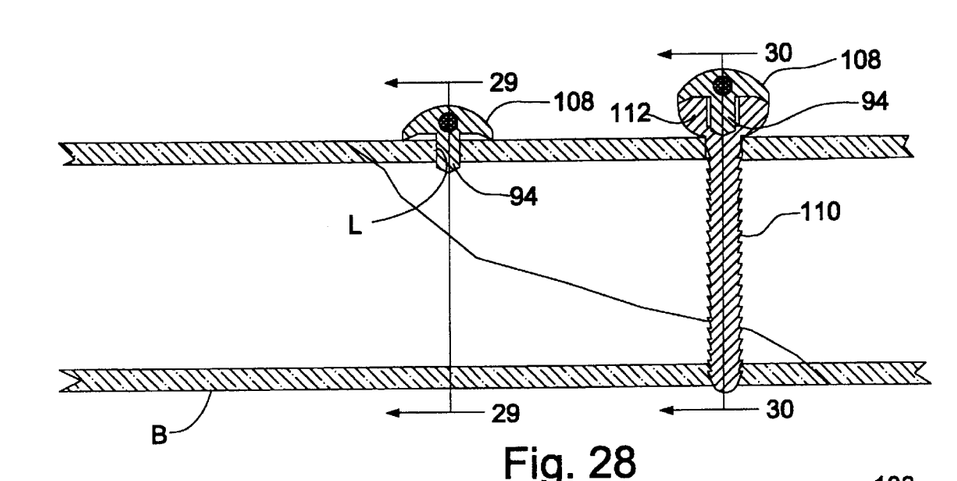
FIG. 28 is a sectional view similar to FIG. 23, but showing one of the embodiments of FIG. 23, less the compression plate.
Figure 29:
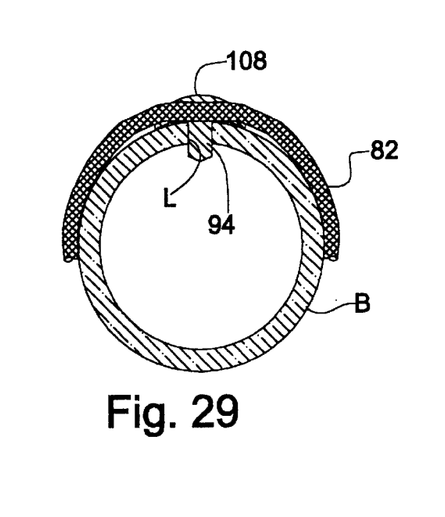
FIG. 29 is a sectional view of the assembly of FIGS. 27 and 28, taken along line 29—29 of FIG. 28.
Figure 30:
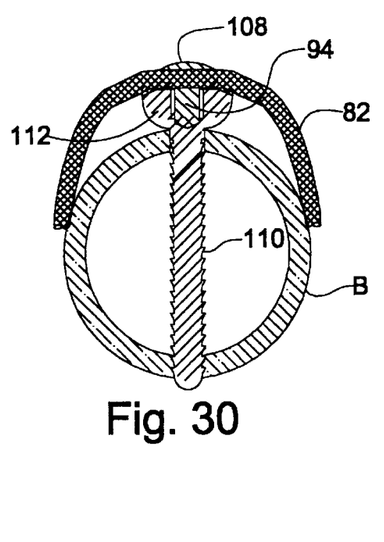
FIG. 30 is a sectional view of the assembly of FIGS. 27 and 29, taken along line 30—30 of FIG. 28.

Referring to FIGS. 27–30, it will be seen that the previously described assembly including adapter 108 may be used in conjunction with cable 82 and crimp device 102, without compression plate 80. As shown in FIGS. 27, 28 (left hand side), and 29, the adapter protrusion 94 may be advanced directly into a hole L in bone B. Alternatively, as shown in FIGS. 27, 28 (right hand side), and 30, the adapter 108 may be used with fixation screw 110, similarly to the arrangement shown in FIG. 25, but without compression plate 80.

There is thus provided an improved assembly, including a fastener device, which may be provided in the form of a crimp device, or as an adapter, and cables, and, optionally, metal compression plates, fixation screws, and independent cable fixing means.

It is to be understood that the present invention is by no means limited to the particular constructions herein disclosed and/or shown in the drawings, but also comprises any modifications or equivalents within the scope of the claims.

What is claimed is:

1. A surgical fastener assembly for use in bone fracture fixation, said assembly comprising:
    a compression plate;
    a surgical cable;
    an adapter for disposition on said compression plate and for receiving said cable, said adapter comprising a head portion having at least one bore extending therethrough for receiving said cable, and a protrusion extending from an underside of said head portion centrally of said head portion for engaging said compression plate, wherein said protrusion comprises:
        a bulbous portion adapted for disposition in a recess in said compression plate, said bulbous portion depending from said head portion; and
        a cylindrical portion adapted for disposition in a screw hole of said compression plate; and
    a discrete crimp device for fixing said cable in position around a bone.

2. A surgical fastener assembly in accordance with claim 1 wherein said bore extends entirely through said head portion side-to-side.

3. A surgical fastener assembly in accordance with claim 1 wherein said bulbous portion is circular in widthwise cross-section and said cylindrical portion is circular in widthwise cross-section and is centered in said bulbous portion and depends from said bulbous portion, such that said protrusion permits rotation of said fastener assembly in said recess and screw hole of said compression plate.

4. A surgical fastener assembly in accordance with claim 1, wherein said crimp device is deformed upon said cable to hold said cable in said crimp device.

5. A surgical fastener assembly in accordance with claim 1 wherein said compression plate, said surgical cable, said adapter, and said crimp device are of electrochemically compatible material.

6. A surgical fastener assembly in accordance with claim 5 wherein said material is metal.

7. A surgical fastener assembly in accordance with claim 6 wherein said metal is stainless steel.

8. A surgical fastener assembly for use in bone fracture fixation, said assembly comprising:
    a compression plate;
    a surgical cable;
    an adapter for disposition on said compression plate and for receiving said cable, said adapter comprising a head portion having at least one bore extending therethrough for receiving said cable, and a protrusion extending from an underside of said head portion centrally of said head portion for engaging said compression plate; and
    a discrete crimp device for fixing said cable in position around a bone,
    wherein said assembly includes a fixation screw and said protrusion comprises a cylindrical portion adapted for disposition in a hole in a head portion of said fixation screw.

9. A surgical fastener assembly device in accordance with claim 8 wherein said adapter head portion has therein a recess for receiving the fixation screw head portion.

10. A surgical fastener assembly in accordance with claim 8 wherein said compression plate, said surgical cable, said fixation screw, said crimp device, and said adapter are of electrochemically compatible material.

11. A surgical fastener assembly in accordance with claim 10 wherein said material is metal.

12. A surgical fastener assembly in accordance with claim 11 wherein said metal is stainless steel.

13. A surgical fastener assembly in accordance with claim 8 wherein said adapter protrusion cylindrical portion is rotatable in said hole in said head portion of said fixation screw.

14. A surgical fastener assembly for use in bone fracture fixation, said assembly comprising:
    a compression plate, said compression plate having a screw hole recess therein and a screw hole in said recess and extending through said plate;
    a surgical cable;
    an adapter for disposition on said compression plate and for receiving said cable, said adapter comprising a head portion having at least one bore extending therethrough for receiving said cable, and a protrusion extending from an underside of said head portion centrally of said head portion for engaging said compression plate, said protrusion being disposed in said screw hole recess and said screw hole; and
    a discrete crimp device for fixing said cable in position around a bone.

15. A surgical fastener assembly for use in bone fracture fixation, said assembly comprising:
    a compression plate, said compression plate having a screw hole recess therein and a screw hole in said recess and extending through said plate;

a screw having a head portion disposed in said recess and a shaft portion extending through said screw hole, said head portion having a hole therein;

a surgical cable;

an adapter for disposition on said compression plate and for receiving said cable, said adapter comprising a head portion having at least one bore extending therethrough for receiving said cable, and a protrusion extending from an underside of said head portion centrally of said head portion for engaging said compression plate, said protrusion extending into said hole; and a discrete crimp device for fixing said cable in position around a bone.

16. A surgical fastener assembly for use in bone fracture fixation, said assembly comprising:

a surgical cable;

an adapter for disposition on the fractured bone and for receiving said cable, said adapter comprising a head portion having at least one bore extending therethrough for receiving said cable, and a protrusion extending from an underside of said head portion centrally of said head portion for engaging a hole in a bone, wherein said assembly includes a fixation screw and said protrusion comprises a cylindrical portion adapted for disposition in a hole in a head portion of said fixation screw; and a discrete crimp device for fixing said cable in position around the bone.

17. A surgical fastener assembly in accordance with claim 16 wherein said bore extends entirely through said head portion side-to-side.

18. A surgical fastener assembly in accordance with claim 16 wherein said adapter head portion has therein a recess for receiving the fixation screw head portion.

19. A surgical fastener assembly in accordance with claim 16, wherein said crimp device is deformed upon said cable to hold said cable in said crimp device.

20. A surgical fastener assembly in accordance with claim 16 wherein said surgical cable, said adapter, and said crimp device are of electrochemically compatible material.

21. A surgical fastener assembly in accordance with claim 20 wherein said material is metal.

22. A surgical fastener assembly in accordance with claim 21 wherein said metal is stainless steel.

23. A surgical fastener assembly in accordance with claim 16 wherein said adapter protrusion cylindrical portion is rotatable in said hole in said head portion of said fixation screw.

24. A method for binding together first and second bone portions, the method comprising the steps of:

providing an adapter device having a head portion with at least one bore extending therethrough, and a protrusion extending from an underside of said head portion centrally of said head portion;

providing a compression plate having a recess therein and a screw hole in said recess and extending through said plate;

providing a surgical cable;

providing a crimp device;

placing said bone portions in position for binding together;

placing said plate alongside said bone portions and abutting said bone portions, and placing said protrusion in said plate recess and screw hole, and encircling the bone portions with said cable, extending said cable through said adapter device bore and said crimp device, pulling said cable taut, and fixing said cable in place by crimping said crimp device.

25. A method for binding together first and second bone portions, the method comprising the steps of:

providing an adapter device having a head portion with at least one bore extending therethrough, and a protrusion extending from an underside of said head portion centrally of the head portion;

providing a compression plate having a recess therein and a screw hole in said recess and extending through said plate;

providing a surgical cable;

providing a fixation screw having a head portion and an axially extending hole in said head portion;

providing a crimp device;

placing said bone portions in position for binding together;

placing said plate alongside said bone portions and abutting said bone portions;

advancing said screw through said plate recess and screw hole and into said bone until a head portion of said screw nests in said plate recess;

placing said adapter device protrusion in said hole in said head portion of said screw;

encircling the bone portions with said cable and extending said cable through said adapter device bore and through said crimp device;

pulling said cable taut; and fixing said cable in place by crimping said crimp device.

26. A method for binding together first and second bone portions, the method comprising the steps of:

providing an adapter device having a head portion with at least one bore extending therethrough, and a protrusion extending from an underside of said head portion centrally of said head portion;

providing a surgical cable;

providing a crimp device;

placing said bone portions in position for binding together;

placing said protrusion in a hole in a bone portion, and encircling the bone portions with said cable, extending said cable through said adapter device bore and said crimp device, pulling said cable taut, and fixing said cable in place by crimping said crimp device.

27. A method for binding together first and second bone portions, the method comprising the steps of:

providing an adapter device having a head portion with at least one bore extending therethrough, and a protrusion extending from an underside of said head portion centrally of the head portion;

providing a surgical cable;

providing a fixation screw having a head portion and an axially extending hole in said head portion;

providing a crimp device;

placing said bone portions in position for binding together;

advancing said screw into the bone until a head portion of said screw abuts the bone;

placing said adapter device protrusion in said hole in said head portion of said screw;

encircling the bone portions with said cable and extending said cable through said adapter device bore and through said crimp device;

pulling said cable taut; and fixing said cable in place by crimping said crimp device.

* * * * *